(12) United States Patent
Mutschler-Chu

(10) Patent No.: US 8,575,450 B2
(45) Date of Patent: Nov. 5, 2013

(54) METHODS AND COMPOSITIONS FOR ACYLSUGARS IN TOMATO

(75) Inventor: Martha A. Mutschler-Chu, Ithaca, NY (US)

(73) Assignee: Cornell University, Ithaca, NY (US)

( * ) Notice: Subject to any disclaimer, the term of this patent is extended or adjusted under 35 U.S.C. 154(b) by 333 days.

(21) Appl. No.: 12/756,925

(22) Filed: Apr. 8, 2010

(65) Prior Publication Data

US 2010/0263067 A1    Oct. 14, 2010

Related U.S. Application Data

(60) Provisional application No. 61/168,061, filed on Apr. 9, 2009.

(51) Int. Cl.
 A01H 1/00   (2006.01)
 C07H 21/04  (2006.01)
 C07K 14/415 (2006.01)

(52) U.S. Cl.
 USPC ....... 800/317.4; 435/411; 530/370; 536/23.1; 800/260

(58) Field of Classification Search
 USPC ............... 435/411, 468; 530/370; 536/23.6; 800/317.4; 426/106, 615
 See application file for complete search history.

(56) References Cited

U.S. PATENT DOCUMENTS

| 4,745,186 | A | 5/1988 | Mudd et al. |
| 4,943,563 | A | 7/1990 | Mutschler et al. |
| 5,260,281 | A | 11/1993 | Pittarelli et al. |
| 5,661,181 | A | 8/1997 | Mutschler et al. |
| 2005/0289674 | A1* | 12/2005 | Ortega Fernandez ...... 800/317.4 |
| 2008/0234386 | A1 | 9/2008 | Spooner-Hart et al. |
| 2009/0217405 | A1* | 8/2009 | Levin et al. .................. 800/260 |

FOREIGN PATENT DOCUMENTS

WO    WO 2008/064413 A8    6/2008

OTHER PUBLICATIONS

Saeidi et al., Euphytica, Mar. 2007, 154(1-2), 231-238.*
Hartman et al., Plant Breeding, Dec. 1999, 118(6), 531-536.*
Mutschler et al., Theoretical and Applied Genetics, 1996, 92(6), 709-718.*
Mutschler-Chu, "Tomato and onion breeding and genetics, 2004 Impact statement", © 2003-2007. The submitted copy is retrieved from the following website address on Dec. 14, 2010: http://vivo.cornell.edu/impact/individual/vivo/individual16573.
Mutschler-Chu et al., "Rapid generation and characterization of tomato lines with acylsugar mediated broad spectrum insect resistance.", *2006 Tomato Breeders Round Table & Tomato Quality Workshop*, p. 25, May 7-11, 2006, Tampa, Florida USA. Cover and index pages are included.
Goffreda, J.C., et al., "Association of Epicuticular Sugars with Aphid Resistance in Hybrids with Wild Tomato", *J. Amer. Soc. Hort. Sci.* 115(1):161-165, 1990.
Goffreda, Joseph C., et al., "Chimeric Tomato Plants Show that Aphid Resistance and Triacylglucose Production are Epidermal Autonomous Characters", *The Plant Cell*, vol. 2, Jul. 1990, pp. 643-649.
Lawson, Darlene M., et al., "Marker-assisted transfer of acylsugar-mediated pest resistance from the wild tomato, *Lycopersicon pennellii*, to the cultivated tomato, *Lycopersicon esculentum*", *Molecular Breeding*, 1997, vol. 3, pp. 307-317.
Resende, J.T.V., et al., "Inheritance of acylsugar contents in tomatoes derived from an interspecific cross with the wild tomato *Lycopersicon pennellii* and their effect in spider mite repellence", Gen. Mol. Res., 2002, 1(2):106-116.
Rodriguez, A.E., "Acylsugars of *Lycopersicon pennellii* Deter Settling and Feeding of the Green Peach Aphid (Homoptera: Aphididae)", *J. Econ. Entomol.*, 1993, vol. 86(1), pp. 34-39.
ScienceDaily® Science News, "Wild Tomatoes Yield Formula for Nontoxic Insect Repellent, Cornell Researchers Say", Nov. 1997, 2 pages. Author unlisted.
Shapiro, Joseph A., et al., "Acylsugars of the Wild Tomato *Lycopersicon pennellii* in Relation to Geographic Distribution of the Species", *Biochemical Systematics and Ecology*, vol. 22, No. 6, 1994, pp. 545-561.

* cited by examiner

*Primary Examiner* — Phuong Bui
(74) *Attorney, Agent, or Firm* — MacMillan, Sobanski & Todd, LLC

(57) ABSTRACT

The present invention relates to tomato plants with increased concentrations of acylsugars, in particular increased concentrations of acylglucoses and/or acylsucroses. The present invention also provides methods for controlling thrips on tomato plants through the use of increased concentrations of acylsugars.

4 Claims, No Drawings

METHODS AND COMPOSITIONS FOR ACYLSUGARS IN TOMATO

CROSS REFERENCE TO RELATED APPLICATIONS

This application claims priority under 35 U.S.C. §119 from U.S. Application Ser. No. 61/168,061, filed Apr. 9, 2009, which is incorporated herein in its entirety by reference.

BACKGROUND OF THE INVENTION

The present invention relates to methods for providing tomato plants with increased levels of acylsugars, methods for controlling pests in tomato, and tomato plants with acylsugars. All publications cited in this application are herein incorporated by reference.

Fruit and vegetable plants are attacked by a variety of insect pests that cause losses directly through feeding on leaves, flowers, fruit, and vegetables, and indirectly through the transmission of viruses, resulting in reduction in yield and fruit/vegetable quality. Pest control products are becoming more expensive and narrower in spectrum, which could result in the need for more sprays or the use of combinations of chemicals. In addition, the loss of label can eliminate the use of some pest control products for certain fruit or vegetable plants. Alternative methods of pest control are needed.

The development of sustainable, environmentally benign methods of crop protection is an important priority in agricultural research. A variety of insects attack crops, causing damage and reducing yields and crop quality. Insects cause crop loss directly through feeding on leaves, flowers, fruit, or seed. A subset of insects damages crops indirectly, through transmission of plant viruses, resulting in reduced yield and crop quality. Breeding for disease resistance has been an important strategy for protection of crops against fungal, bacterial, or viral diseases.

Although integrated pest management (IPM) strategies have been implemented with noted success, insect control has more often relied on the use of pesticides, leading to the evolution of pesticide-resistant insects and to increasing health and environmental concerns. The development of pest resistant plants is an attractive alternative strategy for the control of insects and the direct damage they cause.

Host/insect interactions for plant protection were originally classified as being due to antibiosis, nonpreference, or tolerance (Painter, 1958; Beck, 1965), although the term "antixenosis" was suggested as a more accurate term than nonpreference (Kogan and Ortman, 1978). Under antibiosis a resistant plant exerts an adverse effect on the growth and survival of the insect. Antibiosis can be due to physical characteristics of the plant or due to secondary metabolites such as toxins. Under antixenosis (non-preference), a plant exerts influences on insect behavior, deterring the insect from using the plant as a host (Painter, 1958; Beck, 1965), hence the use of the term "deterrence" in some references. "Tolerance" indicates that the pest is neither deterred from the host plant nor adversely affected by the host plant, but the damage resulting from the pest infestation is reduced compared to that suffered by susceptible varieties of the crop (Painter, 1958; Beck, 1965; Reese et al., 1994). These systems of insect resistance may not be mutually exclusive. It is possible that a resistance mechanism could have aspects of both antibiosis and deterrence.

Breeding for insect resistance has a long history, although insect resistance has been used less than disease resistance in most crops. The wheat variety "Underhill" was reported to have Hessian fly resistance in 1782. Despite resistance breakdown over the years in a number of Hessian fly resistance sources, many wheat varieties have been bred to include this trait (Panda and Khush, 1995; Everson and Gallun, 1980). Another historical example is grape phylloxera (*Daktulosphaira vitifoliae*), a North American aphid that was inadvertently transferred to France about 1860. Grape phylloxera feeds on grape roots, resulting in decreased productivity and vine death. Wild North American grape possessed natural resistance to the pest. This resistance was transferred to develop phylloxera resistant rootstocks that saved the French wine industry. Rootstocks with similar resistance are still in use (Granett et al., 2001).

Some systems of natural insect resistance are based upon physical structures or characteristics. A resistance to potato leafhopper (*Empoasca fabae*) in bean (*Phaseolus vulgaris*) is due to a high density of hooked nonglandular trichomes. These trichomes act as physical barriers, entrapping nymphs as their hooks become embedded in the nymphs' bodies (Pillemer and Tingey, 1976, 1978). The waxy surface of plants has also been implicated in reducing insect infestation. "Glossy" mutants, lacking the normal waxy layer or "bloom" of non-mutant plants, have been found in a number of crop species. Sadasivan and Thayumanavan (2003) list instances in *Brassica*, raspberry, castor, sorghum, wheat, sugarcane, and onion in which the glossy plants are more susceptible to a variety of insect pests than the normal waxy plants. This could be due to adverse effects of the waxy layer on the ability of insects to adhere, move, or feed on the plant. Differences in wax layer may also affect the choice of the plant for feeding or oviposition. Consequently, such waxy surfaces may confer either antibiosis or antixenosis depending on their mode of action against different pests.

A number of insect resistance systems are based upon secondary metabolites that are toxic or otherwise detrimental or noxious to pests. Secondary metabolites are a very diverse array of compounds that are produced by plants but which are not considered essential for basic metabolic function or processes. There are too many secondary metabolites to describe in any detail here (see Hadacek, 2002; Singer et al., 2003; Sadasivan and Thayumanavan, 2003), but a few well-known examples are 2-tridecanone, cucurbitacins, and glycoalkaloids.

The 2-tridecanone, a methyl ketone, is a secondary metabolite in glandular trichomes that is the basis of insect resistance in *Lycopersicon hirsutum* var. *glabratum* (Williams et al., 1980; Fery and Kennedy, 1987). 2-tridecanone has been implicated in the resistance of *L. hirsutum* to tobacco hornworm (*Manduca sexta*), spider mite species (*Tetranychus* spp.), Colorado potato beetle (*Leptinotarsa decemlineata*), tomato pinworm (*Keiferia lycopersicella*), and beet armyworm (*Spodoptera exigua*) (Kennedy, 1976; Gonyalves et al., 1998; Farrar and Kennedy, 1991; Lin et al., 1987; Maluf et al., 1997). This compound is quite toxic, and also acts as an oviposition and/or feeding deterrent.

The plant species *L. pennellii* Corr. is a wild relative of the cultivated tomato, *L. esculentum*. As a plant species, *L. pennellii* is morphologically intermediate between potato and tomato. However, since *L. pennellii* is interfertile in controlled pollinations with the cultivated tomato, it is commonly grouped with other wild species of tomato.

Physical entrapment of arthropods by the exudate from glandular hairs of various plants is known in wild *Solanum* species such as *S. berthaultii*, *S. tarijense*, and *S. polyadenium*. The exudate of the four-lobed (type A) trichomes, when exposed to atmospheric oxygen, forms a viscous substance which accumulates on the tarsi and mouthparts of green peach aphid (*Myzus persicae* Sulzer), the potato aphid (*Macrosiphum euphorbiae* Thomas), and the potato leafhopper (*Empoasca fabae* Harris). The viscous material hardens and effectively immobilizes the insects, resulting in their death through starvation. *S. berthaultii* also possesses a second type of glandular trichome (type B) which is slender and continuously secretes a sticky substance at its tip. This type of trichome has been found to be important in entrapping the two-spotted spider mite (*Tetranychus urticae* Koch) and tarsonemid mites. Mites are not powerful enough to rupture the membrane of the four-lobed glandular trichomes. Utilizing an electronic feeding monitor, Lapointe and Tingey (1984) demonstrated that aphid feeding on *S. berthaultii* leaves was characterized by a delay in probing, a decrease in the duration of probes, and that an overall physical removal of the type B exudate resulted in a decrease of resistance as measured by these parameters.

The most abundant of the types of glandular hairs in the genus *Lycopersicon* are the type IV and VI trichomes. The type VI trichome is similar in appearance to the type A trichomes on *Solanum* species while the type IV trichome is similar to the type B of *Solanum*. Physical entrapment of the carmine spider mite (*Tetranychus cinnabarinus* Boisduval), the two-spotted spider mite (*T. urticae*), and the greenhouse whitefly (*Trialeurodes vaporariorum* Westwood) by type IV glandular exudate appears to be the principal component of resistance to these pests by certain *Lycopersicon* species (Gentile et al., 1969, 1968). Removal of the exudate with alcohol resulted in successful oviposition and normal nymphal development of the greenhouse whitefly (Gentile et al., 1968). The release of a viscous exudate upon rupture of the type VI trichomes is suggested as the basis for physical entrapment of insects in several wild tomato species.

*L. pennellii*, especially accession LA716, is resistant to several insect species, including greenhouse whitefly, carmine and two-spotted spider mites, and potato and green peach aphids. Insect resistance in *L. pennellii* is attributed to the type IV glandular hairs, which are not present on the foliage of *L. esculentum*. Resistance to greenhouse whitefly has been attributed to the entrapment of adults in the sticky exudate of type IV trichomes (Gentile et al., 1968). Physical entrapment of carmine and two-spotted spider mites and potato aphids in exudate of type IV trichomes was also suggested as the mode of resistance to these pests (Gentile et al., 1969, Gentile and Stoner, 1968b). Clayberg (1975) observed that a periclinal chimera, consisting of the epidermis, with dense indumentum of *L. pennellii* and a "core" of *L. esculentum* origin, had levels of whitefly resistance equal to that in *L. pennellii* but a reduced level of resistance to potato aphids.

The type IV trichome of *L. pennellii*, its hybrids and progeny are slender hairs with pointed tips about 0.2 mm to 0.4 mm in length, standing on a large simple basal cell. The hair is glandular and it continuously secretes a droplet which is not membrane-bound. Further details of these trichomes may be found in Luckwill (1943). The exudate of the type IV trichomes of *L. pennellii*, its hybrids, and progeny is composed of a complex mixture of glucose triesters of saturated straight chain and branched fatty acids (Burke et al., 1987). The most abundant fatty acids found in *L. pennellii* glucose esters include 2-methylpropanoic, 8-methylnonanoic, and n-decanoic acids, with 2-methylbutanoic, 3-methylbutanoic, and n-dodecanoic acids being present in relatively minor amounts. The positions of esterification have all been found to be the 2, 3, and 4 positions.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The development of new tomato cultivars requires the development and selection of tomato varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Having a morphology that is intermediate between potato and tomato means that *L. pennelli* is horticulturally unsuitable for either home or commercial production of tomatoes. Cultivated tomatoes lack the high concentration and types of acylsugars of *L. pennellii* and therefore lack the multiple pest resistance of *L. pennellii*.

SUMMARY OF THE INVENTION

The following embodiments and aspects thereof are described in conjunction with systems, tools, and methods which are meant to be exemplary, not limiting in scope. In various embodiments, one or more of the above-described problems have been reduced or eliminated, while other embodiments are directed to other improvements.

The present invention provides a method for combining the multiple pest resistance of *L. pennellii* with the desirable horticultural traits of cultivated tomato. In addition, the present invention provides the resulting tomato plant comprising the multiple pest resistance of *L. pennellii* with the desirable horticultural traits of cultivated tomato.

The invention includes tomato plants that are hybrid plants of tomato varieties of species *L. esculentum* and the related species *L. pennellii* having elevated levels of acylsugars.

The invention embodies *L. esculentum*×*L. pennellii* hybrid plants having resistance to invertebrate pests including, but not limited to, thrips (of the insect Order Thysanoptera); fruitworm (*Helicoverpa*, formerly *Heliothis zea*); tomato pinworm (*Keiferia lycopersicella*); beet armyworm (*Spodoptera exigua*); silverleaf whitefly (*B. tabaci* biotype B); leafminer (*Liriomyza* spp); potato aphid (*Macrosiphum euphorbiae*); and green peach aphid (*Myzus persicae*). Such resistance furthermore provides as a consequence resistance to various plant viruses that tend to gain access to plants via damage caused by the action of the aforementioned invertebrate pests, or pests like them.

In addition to the exemplary aspects and embodiments described above, further aspects and embodiments will become apparent by study of the following descriptions.

Definitions

In the description and tables that follow, a number of terms are used. In order to provide a clear and consistent understanding of the specification and claims, including the scope to be given such terms, the following definitions are provided:

97FL. As used herein, 97FL refers to a specific plant produced by crossing a cultivated tomato plant with *L. pennillii* accession LA716 to produce a hybrid tomato plant with a very high level of acylsugars.

Acylglucose. As used herein, acylglucose refers to any of a group of sugars comprising glucose acylated with short and/or medium chain-length fatty acids varying in length.

Acylsucrose. As used herein, acylsucrose refers to any of a group of sugars comprising sucrose acylated with short and/or medium chain-length fatty acids varying in length.

Acylsugar. As used herein, acylsugar refers to any of a group of 2, 3, 4-tri-O-acylhexopyranoses including 2,3,4-tri-O-acylglucoses, 3',3,4-tri-O-acylsucroses and 3',3,4,6-tetra-O-acylsucroses, with a range of odd and even short-to-medium-chain length fatty acid constituents.

Acylsugar line. As used herein, acylsugar line refers to any of a group of plants produced by crossing a cultivated tomato plant with an *L. pennelli* plant or by crossing, selfing, or backcrossing progeny of a cross between a cultivated tomato plant with an *L. pennellii* plant.

Allele. An allele is any of one or more alternative forms of a gene which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. Backcrossing is a process in which a breeder repeatedly crosses hybrid progeny back to one of the parents, for example, a first generation hybrid $F_1$ with one of the parental genotypes of the $F_1$ hybrid.

Commercially acceptable. Commercially acceptable means a tomato plant or plant hybrid having traits such as seed yield, fruit yield, emergence, vigor, vegetative vigor, disease resistance, and seed set, which results in a commercially marketable product.

FLA-47. As used herein, FLA-47 refers to a specific standard cultivated tomato plant having the typical tomato concentration of acylsugars and is used as a control in acylsugar trials.

Gene. As used herein, "gene" refers to a segment of nucleic acid. A gene can be introduced into a genome of a species, whether from a different species or from the same species, using transformation or various breeding methods.

Gene Silencing. The interruption or suppression of the expression of a gene at the level of transcription or translation.

Genotype. Refers to the genetic constitution of a cell or organism.

Grown outside. Refers to plants not grown in a greenhouse or growth chamber. A plant grown in an outdoor environment.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism, and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two varieties. Percent identity is determined by comparing a statistically significant number of the homozygous alleles of two developed varieties. For example, a percent identity of 90% between variety 1 and variety 2 means that the two varieties have the same allele at 90% of their loci.

Percent Similarity. Percent similarity as used herein refers to the comparison of the homozygous alleles of a variety with another plant, and if the homozygous allele of variety 1 matches at least one of the alleles from the other plant then they are scored as similar. Percent similarity is determined by comparing a statistically significant number of loci and recording the number of loci with similar alleles as a percentage. A percent similarity of 90% between variety 1 and another plant means that variety 1 matches at least one of the alleles of the other plant at 90% of the loci.

Plant. As used herein, the term "plant" includes reference to an immature or mature whole plant, including a plant from which seed or anthers have been removed. A seed or embryo that will produce the plant is also considered to be the plant.

Plant Parts. As used herein, the term "plant parts" (or a tomato plant, or a part thereof) includes, but is not limited to, protoplasts, callus, leaves, stems, roots, root tips, anthers, pistils, seed, fruit, embryo, pollen, ovules, cotyledon, hypocotyl, flower, shoot, tissue, petiole, cells, meristematic cells, and the like.

Progeny. As used herein, progeny includes an $F_1$ tomato plant produced from the cross of two tomato plants or from the cross of a tomato plant with an *L. pennellii* plant. Progeny further includes, but is not limited to, subsequent $F_2$, $F_3$, $F_4$, $F_5$, $F_6$, $F_7$, $F_8$, $F_9$ and $F_{10}$ generational crosses with the recurrent parental line.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Tomato or cultivated tomato. As used herein, tomato or cultivated tomato means a member of *Lycopersicon esculentum* (Mill.) which is commonly referred to as tomato.

Total acylglucose percent. The proportion of total acylsugars that is composed of acylglucose.

Total acylsugar concentration. The amount per unit mass of plant tissue of all forms of acylsugar molecules present in that plant tissue.

DETAILED DESCRIPTION OF THE INVENTION

The present invention provides a method for combining the multiple pest resistance of *L. pennellii* with the desirable horticultural traits of cultivated tomato. In addition, the present invention provides the resulting tomato plant comprising the multiple pest resistance of *L. pennellii* with the desirable horticultural traits of cultivated tomato.

The invention includes tomato plants that are hybrid plants of tomato varieties of species *L. esculentum* and the related species *L. pennellii* having elevated levels of acylsugars.

The present invention embodies *L. esculentum*×*L. pennellii* hybrid plants having resistance to invertebrate pests including, but not limited to, thrips (of the insect Order Thysanoptera); fruitworm (*Helicoverpa*, formerly *Heliothis zea*); tomato pinworm (*Keiferia lycopersicella*); beet armyworm (*Spodoptera exigua*); silverleaf whitefly (*B. tabaci* biotype B); leafminer (*Liriomyza* spp); potato aphid (*Macrosiphum euphorbiae*); and green peach aphid (*Myzus persicae*). Such resistance furthermore provides as a consequence resistance to various plant viruses that tend to gain access to plants via damage caused by the action of the aforementioned invertebrate pests, or pests like them.

According to the present invention, there is provided a tomato plant having a dried leaf tissue total acylsugar concentration of between 13.0 µmol/mg and 47.0 µmol/mg.

In another aspect of the present invention, there is provided a tomato plant having a dried leaf tissue total acylglucose concentration of between 30.0% and 41.0% of the total acylsugar concentration when grown outside.

In yet another aspect of the present invention, there is provided a method to control pests, wherein the method comprises growing a tomato plant having a dried leaf tissue total acylsugar concentration of between 13.0 µmol/mg and 47.0 µmol/mg.

In another embodiment of the invention a tomato plant is provided that has a dried leaf tissue total acylsugar concentration of between 13.0 µmol/mg and 25.9 µmol/mg.

In still another aspect of the invention a tomato plant is provided that has a dried leaf tissue total acylsugar concentration of between 26.0 µmol/mg and 35.9 µmol/mg.

In another embodiment of the present invention a tomato plant is provided that has a dried leaf tissue total acylsugar concentration of between 36.0 µmol/mg and 47.0 µmol/mg.

In another aspect of the present invention, there is provided a method to control insects.

In another aspect of the invention, there is provided a method to control thrips.

In another aspect of the invention, there is provided a method to control viruses.

In another embodiment of the present invention, there is provided a tomato plant that is commercially acceptable.

In another aspect of the present invention, there is provided a tomato plant having a dried leaf tissue total acylglucose concentration of between 30.0% and 41.0% of the total acylsugar concentration when grown outside.

In another embodiment of the invention, there is provided a tomato plant having a dried leaf tissue total acylglucose concentration of between 30.0% and 33.9% when grown outside.

In yet another embodiment of the present invention, there is provided a tomato plant having a dried leaf tissue total acylglucose concentration of between 34.0% and 37.9% when grown outside.

In still another embodiment of the present invention, there is provided a tomato plant having a dried leaf tissue total acylglucose concentration of between 38.0% and 41.0% when grown outside.

In another embodiment of the invention, there is provided a method to control insects, wherein the method comprises growing the tomato plant.

In another aspect of the invention, there is provided a method to control thrips, wherein the method comprises growing the tomato plant.

In yet another aspect of the present invention, there is provided a method to control viruses, wherein the method comprises growing the tomato plant.

In still another aspect of the present invention, there is provided a tomato plant, wherein said tomato plant is commercially acceptable.

In another embodiment of the present invention, there is provided a method of producing a hybrid tomato seed comprising crossing the plant of the invention with another tomato plant.

In another aspect of the invention, there is provided a tomato hybrid seed.

In another aspect of the present invention, there is provided a method of producing a hybrid seed comprising crossing the plant having a dried leaf tissue total acylglucose concentration of between 30.0% and 41.0% of the total acylsugar concentration with another tomato plant.

In still another embodiment of the present invention, there is provided the hybrid seed produced by the method of crossing the plant having a dried leaf tissue total acylglucose concentration of between 30.0% and 41.0% of the total acylsugar concentration with another tomato plant.

EXAMPLES

In the following Examples, the results of crossing *L. esculentum* and *L. pennellii* to yield hybrid plants is shown as the initial step in the introduction of the acylsugar trait into tomato plants. Beginning observations are shown in Example 1 for tests conducted in Florida in 2007. The cultivated tomato line used for comparison is called FLA-47. A variety of hybrid lines were obtained in crosses with *L. pennellii*, with the line designated 97FL having the highest acylsugar content in a range of acylsugar levels. Table 1 shows these tomato hybrid lines and the acylsugar levels observed in comparison to FLA-47. The hybrid lines were tested for their ability to reduce infestation by progressive developmental stages of silverleaf whitefly. These tests are shown in Tables 2a-2d. The overall observation from these studies is the correlation between unexpected elevated acylsugar content versus control line FLA-47 in the hybrid plants, and reduced infestation of plants by silverleaf whitefly at all developmental stages examined.

Example 2 includes an expanded set of 31 acylsugar lines, crosses of acylsugar lines to tomato, and crosses of acylsugar lines to other acylsugar lines, compared to 5 cultivated tomato lines. This larger comparison was conducted in New York in 2006. All of the crossed lines show higher mean acylsugar content than the cultivated tomato controls.

The acylsugar contents of hybrid plant lines produced in various breeding experiments are shown in Example 3. These crosses include hybrids produced when the male parent is from the high acylsugar line 97FL (Table 4), hybrids produced by crosses of acylsugar lines (Table 5), crosses having *L. pennellii* (line LA716) as the male parent (Table 6), and a comparison of hybrids having either 97FL or LA716 as the male parent (Table 7). The data underscore the important contribution to acylsugar content by *L. pennellii* introgressions in hybrid lines, and show the correspondence between high acylglucose as a proportion of total acylsugars and high total acylsugars.

The unexpected effects of *L. pennellii* introgressions in tomato lines and the increase in acylsugar content in selfed generations of tomatoes is demonstrated in Example 4. Tables 8 and 9 display acylsugar levels (specifically, acylsucrose) compared between progeny and parental lines for two different $F_2$ populations. Both $F_2$ populations had significantly higher acylsucrose levels than the parental lines.

Example 5 addresses observations that higher acylsugars are associated with certain QTL related to acylglucose production. Surprisingly, for acylglucoses to be produced, plants must be genetically heterozygous for at least two acylglucose QTL.

The impact of acylsugars on another insect, thrips, and the subsequent influence on tomato spotted wilt virus (TSWV) infection of tomato plants by being transmitted to plants via thrips infestation, is shown in Example 6. Table 10 shows that, although acylsugars are associated with green parts of plants and thrips feed on flowers, thrips infestation is reduced in association with higher levels of acylsugars, resulting in diminished signs of TSWV infection.

Example 7 addresses chromosomal introgressions of *L. pennellii* and particular observations showing that certain introgressions have diminished negative impact on fruit quality and production.

Example 8 shows additional lines developed and examined under greenhouse conditions in 2009. Molecular markers were employed to track the segregation of particular introgressions of *L. pennellii*. The lines show high levels of acylsugars and certain lines were identified as superior breeding lines. The combined acylsugar and molecular analysis of these lines is shown in Table 11.

Example 1

Florida Trials 2006-2007

The initial acylsugar line produced was 97FL. 97FL produces unexpectedly high levels of acylsugars and shows significant reduction of insect infestation in prior field trials. Fingerprinting 97FL using over 150 molecular markers showed that its genome had 9 *L. pennellii* introgressions of varying lengths on chromosomes 2, 3, 4, 5, 6, 7, 8, and 10. As a result, the 97FL genome was 73% tomato and 27% *L. pennellii*. Three of the introgressions are very small (<5 cm) one was moderate (12 cM), and the rest were large to very large (25 to 85 cM). The introgression of so much of the *L. pennellii* genome had detrimental effects on plant type. The large introgressions were associated with negative traits, including reduced and/or delayed fruit set, small fruit size, lack of seed set, reduced plant size, and poor germination. This association is the result of linkage drag: linkage between genes desired (for acylsugar production) and undesirable genes. To eliminate the negative traits, the linkage between the desired and the negative genes was broken through recombination. From 2001 to 2005, the breeding program used a combination of molecular markers and acylsugar screens to select acylsugar producing plants with reductions in the number and sizes of introgressions.

The first trials of acylsugar lines were performed in Florida at the Gulf Coast Research & Education Center in the spring of 2006. These trials demonstrated reduction of silverleaf whitefly infestation on the tomato/*L. pennellii* hybrid lines. The trial was repeated using more tomato/*L. pennellii* hybrid lines with different levels of acylsugars, and increased replications in the trial in the spring of 2007.

Silverleaf whitefly infestation of tomato controls was observed during the season until moderate levels of the pest were found on the susceptible controls, and then data were collected on the full experiment. Data were collected twice: on May 22 and Jun. 18, 2007. For each of these dates, separate counts were made of eggs, first instar, second and third instar, and fourth instar. Acylsugar samples were collected in late May, midway between the two insect count dates.

Table 1 shows the acylsugar concentration of a cultivated tomato (FLA-47) and several tomato/*L. pennellii* hybrid lines in μmol/mg of dried leaf tissue. Column 1 shows the line, column 2 shows the acylsugar concentration in μmol/mg dried leaf tissue and columns 3 through 8 show the statistical relationship between the acylsugar concentrations of the various lines. Levels not connected by same letter are significantly different at 0.05 level.

TABLE 1

Spring 2007 Acylsugar levels

| Line | Mean acylsugar level μmol/mg dried leaf tissue | | | | | |
|---|---|---|---|---|---|---|
| FLA-47 | 5.0 | | | | | F |
| 06.6059.2 | 9.4 | | | | E | |
| 06.6076.8 | 10.0 | | | D | E | |
| 05.5019.140 | 10.2 | | | D | E | |
| 06.6258.7 | 13.4 | | C | D | E | |
| 05.5019.462 | 13.6 | | C | D | | |
| 06.6245.2 | 15.5 | B | C | | | |
| 06.6116.9 | 15.8 | B | C | | | |
| 06.6066.4 | 17.4 | B | C | | | |
| 06.6041.9 | 19.3 | B | | | | |
| 06.6018.1 (97FL) | 46.9 | A | | | | |

As shown in Table 1, a range of acylsugar levels was represented by the tomato/*L. pennellii* hybrid acylsugar lines in the trial, with 97FL having a uniquely high level, close to 47 μmol/mg dry leaf tissue, and the other lines having acylsugar levels ranging from 10 to 20 μmol/mg dry leaf tissue (Table 1). Within these lines, lines 06.6245.2, 06.6116.9, 06.6066.4, 06.6041.9 had the higher range of acylsugar levels (15 to 20 μmol/mg dry leaf tissue), and lines 06.6059.2, 06.6076.8, and 05.5019.140 had significantly lower acylsugar levels (9 to 10 μmol/mg dry leaf tissue). This allowed an initial determination of the affect of acylsugar level on the degree of pest control.

Higher pest levels, and so better discrimination among lines, were observed in the June 18 pest count. The lowest levels of silverleaf whitefly infestation, across developmental stages of this pest, were on 97FL, the line with the highest acylsugar level (Table 2a through 2d). The egg counts showed significant reduction for 97FL and also for the higher acylsugar producers, 06.6066.4, 06.6041.9, 05.5019.462, and 06.6116.9 (Table 2a).

Table 2a shows the number of silverleaf whitefly (SLWF) eggs per leaflet counted on the leaves of a cultivated tomato line (FLA-47) and several tomato/*L. pennellii* hybrid lines comprising the acylsugar concentrations in Table 1. Column 1 shows the line, column 2 shows the mean number of silverleaf whitefly eggs counted on May 22, 2007, columns 3 through 6 show the statistical relationship between the number of eggs found on each line for May 22, column 7 shows the number of silverleaf whitefly eggs counted on Jun. 18, 2007 and columns 9 through 11 show the statistical relationship between the number of eggs found on each line for June 18. Levels not connected by the same letter are significantly different at 0.05 level by Dunnett's test.

TABLE 2a

FL 2007 Numbers of SLWF eggs per leaflet

| Line | Mean egg number on date | | | | | | | | |
|---|---|---|---|---|---|---|---|---|---|
| | MAY 22 | | | | JUNE 18 | | | | |
| FLA-47 | 12.9 | A | | | 8.0 | A | | | |
| 06.6059.2 | 2.4 | | C | D | 4.1 | A | B | | |
| 06.6245.2 | 1.7 | | C | D | 3.5 | A | B | C | |
| 06.6258.7 | 4.0 | | C | D | 3.1 | A | B | | |
| 06.6076.8 | 2.1 | | C | D | 3.0 | A | B | C | |
| 05.5019.140 | 3.1 | | C | D | 2.9 | A | B | C | |
| 06.6066.4 | 6.4 | B | C | | 2.4 | | B | C | D |
| 06.6041.9 | 2.2 | | C | D | 1.7 | | B | C | D |
| 05.5019.462 | 1.6 | | C | D | 1.1 | | B | C | D |
| 06.6116.9 | 1.7 | | C | D | 0.6 | | | C | D |
| 06.6018.1 (97FL) | 0.3 | | | D | 0.0 | | | | D |

Table 2b shows the number of silverleaf whitefly first instars per leaflet counted on the leaves of a cultivated tomato line (FLA-47) and several tomato/*L. pennellii* hybrid lines comprising the acylsugar concentrations in Table 1. Column 1 shows the line, column 2 shows the mean number of silverleaf whitefly first instars per leaflet counted on May 22, 2007, columns 3 through 5 show the statistical relationship between the number of first instars found on each line for May 22, column 6 shows the number of silverleaf whitefly first instars counted on Jun. 18, 2007 and columns 7 through 9 show the statistical relationship between the number of first instars found on each line for June 18. As shown in Table 2b, the $1^{st}$ instar counts showed significant reduction for 97FL and also for the other acylsugar lines. Levels not connected by the same letter are significantly different at 0.05 level by Dunnett's test.

TABLE 2b

FL 2007 Numbers of SLWF $1^{st}$ instar per leaflet

| Line | Mean number $1^{st}$ instar per leaflet on date | | | | | | | |
|---|---|---|---|---|---|---|---|---|
| | MAY 22 | | | | JUNE 18 | | | |
| FLA-47 | 5.1 | A | | | 8.8 | A | | |
| 06.6076.8 | 0.1 | | | C | 2.4 | | B | |
| 06.6258.7 | 0.9 | | | C | 1.5 | | B | C |
| 06.6059.2 | 0.9 | | B | C | 1.3 | | B | C |
| 05.5019.462 | 0.6 | | B | C | 1.2 | | B | C |
| 06.6041.9 | 0.6 | | | C | 1.0 | | B | C |
| 06.6245.2 | 0.3 | | | C | 1.0 | | B | C |
| 06.6066.4 | 1.3 | | B | C | 0.9 | | B | C |
| 05.5019.140 | 1.0 | | B | C | 0.9 | | B | C |
| 06.6116.9 | 1.1 | | | C | 0.5 | | B | C |
| 06.6018.1 (97FL) | 0.0 | | | C | 0.0 | | | C |

Table 2c shows the mean number of silverleaf whitefly second and third instars per leaflet counted on the leaves of a cultivated tomato line (FLA-47) and several tomato/*L. pennellii* hybrid lines comprising the acylsugar concentrations in Table 1. Column 1 shows the line, column 2 shows the mean number of silverleaf whitefly second and third instars per leaflet counted on May 22, 2007, columns 3 through 5 show the statistical relationship between the mean number of second and third instars found on each line for May 22, column 6 shows the number of silverleaf whitefly second and third instars counted on Jun. 18, 2007 and columns 7 through 10 show the statistical relationship between the mean number of second and third instars found on each line for June 18. As shown in Table 2c, the second and third instar counts showed significant reduction for 97FL and also for the higher acylsugar producers, 06.6066.4, 06.6258.7, 06.6245.2, 06.6116.9, and 06.6041.9. Levels not connected by the same letter are significantly different at 0.05 level by Dunnett's test.

TABLE 2c

FL 2007 Numbers of SLWF 2nd/3rd instar per leaflet

| Line | Mean number 2nd/3rd instar per leaflet on date | | | | | | | |
|------|------|---|---|---|------|---|---|---|
|      | MAY 22 | | | | JUNE 18 | | | |
| FLA-47 | 6.3 | A | | | 37.3 | A | | |
| 06.6076.8 | 0.3 | | | C | 3.5 | | B | |
| 05.5019.462 | 0.3 | | | C | 2.6 | | B | C |
| 05.5019.140 | 0.8 | | | C | 2.0 | | B | C |
| 06.6059.2 | 0.6 | | B | C | 1.9 | | B | C |
| 06.6066.4 | 2.6 | | B | C | 1.9 | | | C | D |
| 06.6258.7 | 0.5 | | | C | 1.7 | | B | C |
| 06.6245.2 | 0.7 | | | C | 0.7 | | | | D |
| 06.6116.9 | 0.5 | | | C | 0.6 | | | | D |
| 06.6041.9 | 0.4 | | | C | 0.3 | | | | D |
| 06.6018.1 (97FL) | 0.0 | | | C | 0.0 | | | | D |

Table 2d shows the mean number of silverleaf whitefly fourth instars per leaflet counted on the leaves of a cultivated tomato line (FLA-47) and several tomato/L. pennellii hybrid lines comprising the acylsugar concentrations in Table 1. Column 1 shows the line, column 2 shows the mean number of silverleaf whitefly fourth instars per leaflet counted on May 22, 2007, columns 3 and 4 show the statistical relationship between the mean number of fourth instars found on each line for May 22, column 5 shows the number of silverleaf whitefly fourth instars counted on Jun. 18, 2007 and columns 6 through 9 show the statistical relationship between the mean number of fourth instars found on each line for June 18. As shown in Table 2d, the fourth instar counts showed significant reduction for 97FL and also for the other acylsugar lines. Levels not connected by the same letter are significantly different at 0.05 level by Dunnett's test.

TABLE 2d

FL 2007 Numbers of SLWF $4^{th}$ instar per leaflet

| Line | Mean number 4th instar per leaflet on date | | | | | | |
|------|------|---|---|---|------|---|---|
|      | MAY 22 | | | | JUNE 18 | | |
| FLA-47 | 4.6 | A | | | 72.9 | A | |
| 06.6059.2 | 0.3 | | B | | 2.4 | C | D |
| 05.5019.140 | 0.0 | | B | | 2.1 | C | D |
| 06.6076.8 | 0.0 | | B | | 1.8 | C | |
| 06.6258.7 | 0.1 | | B | | 1.7 | C | D |
| 06.6245.2 | 0.0 | | B | | 1.0 | C | D |
| 05.5019.462 | 0.1 | | B | | 0.7 | C | D |
| 06.6066.4 | 0.1 | | B | | 0.6 | C | D |
| 06.6041.9 | 0.1 | | B | | 0.4 | C | D |
| 06.6116.9 | 0.1 | | B | | 0.2 | | D |
| 06.6018.1 (97FL) | 0.0 | | B | | 0.0 | C | D |

The results of the trials with silverleaf whitefly indicate that moderate levels of control are possible with lower levels of acylsugar comparable to tomato/L. pennellii hybrid lines 06.6066.4 and 06.6041.9, and that nearly no insects were found on tomato/L. pennellii hybrid line 97FL, which had the highest levels of acylsugars. However reduction of acylsugar level to less than that of tomato/L. pennellii hybrid lines 06.6066.4 and 06.6041.9 may result in reduced pest control.

Example 2

2006 Ithaca Trials of Acylsugar Lines, Tomato×Acylsugar Line Hybrids, and Acylsugar Line×Acylsugar Line Hybrids A much larger trial of acylsugar lines, tomato×acylsugar line hybrids, and acylsugar line×acylsugar line hybrids has been conducted in Ithaca, N.Y. Acylsugar samples were collected in late July and analyzed in early August. A set of 31 acylsugar lines was evaluated for acylsugar production and other traits (Table 3). The five tomato lines also included in the field all lack appreciable acylsugars, and show similar baseline readings. A total of 24 of the 31 acylsugar lines have total acylsugar levels significantly higher than that of the tomato controls, but the top 14 to 16 lines have acylsugars at levels expected to control insects based on the prior trials in Florida.

Table 3 shows 5 cultivated tomato lines and 27 tomato hybrid lines comprising varying amounts of L. pennellii introgressions which result in different concentrations of acylsugars. Column 1 shows the number or name of the line, column 2 shows the mean acylsugar concentration in μmol/mg dried leaf tissue and columns 3 through 19 show the statistical relationship between the concentrations in the various lines. Levels not connected by same letter are significantly different,

TABLE 3

Full set of acylsugar lines and their total acylsugar levels in Ithaca Trial

| ID | Mean acylsugar level μmol/mg dried leaf tissue | | | | | | | | | |
|----|------|---|---|---|---|---|---|---|---|---|
| 055019-456 | 34.3 | A | | | | | | | | |
| 055019-462 | 33.7 | A | B | | | | | | | |
| 055018-90 | 28.5 | A | B | C | | | | | | |
| 055018-67 | 28.0 | A | B | C | D | | | | | |
| 66223-6 | 26.2 | | | C | D | E | | | | |
| 071026 | 25.8 | | B | C | D | E | F | | | |
| 055019-404 | 25.8 | | B | C | D | E | F | G | | |
| 055019-36 | 25.3 | | | C | D | E | F | | | |
| 055019-430 | 23.3 | | | C | D | E | F | G | H | |
| 66041-2 | 22.5 | | | C | D | E | F | G | H | |
| 055019-412 | 21.1 | | | | D | E | F | G | H | I |

TABLE 3-continued

Full set of acylsugar lines and their total acylsugar levels in Ithaca Trial

| ID | Mean acylsugar level μmol/mg dried leaf tissue | | | | | | | | | | | |
|---|---|---|---|---|---|---|---|---|---|---|---|---|
| 055019-369 | 20.7 | E | F | G | H | I | | | | | | |
| 66059-2 | 20.1 | E | F | G | H | I | J | | | | | |
| 66019-9 | 18.3 | | F | G | H | I | J | K | | | | |
| 66148-5 | 17.6 | | | G | H | I | J | K | | | | |
| 055018-3 | 17.5 | | F | G | H | I | J | K | L | | | |
| 055019-140 | 16.5 | | | | H | I | J | K | L | | | |
| 66217-6 | 14.9 | | | | H | I | J | K | L | M | N | |
| 66037-8 | 14.6 | | | | | I | J | K | L | M | | |
| 055018-17 | 12.7 | | | | | | J | K | L | M | N | |
| 66046-6 | 12.4 | | | | | | | K | L | M | N | |
| 055018-49 | 12.1 | | | | | | | K | L | M | N | |
| 066254-7 ('071024) | 12.0 | | | | | | | K | L | M | N | |
| 66087-4 | 11.5 | | | | | | | K | L | M | N | |
| 66060-5 | 9.8 | | | | | | | | L | M | N | O |
| 066112-8 ('071021) | 9.8 | | | | | | | | L | M | N | O |
| 066062-7 ('071023) | 9.4 | | | | | | | | L | M | N | O | P |
| 055018-18 | 8.6 | | | | | | | | | M | N | O | P |
| 66286-3 | 8.5 | | | | | | | | | M | N | O | P | Q |
| 055018-5 | 6.5 | | | | | | | | | | N | O | P | Q |
| 055018-14 | 6.4 | | | | | | | | | | N | O | P | Q |
| NC84-173 | 3.6 | | | | | | | | | | | O | P | Q |
| NC33EB-1 (PH-2 + PH-3) | 3.0 | | | | | | | | | | | O | P | Q |
| FLA 595-2 Ty | 2.8 | | | | | | | | | | | O | P | Q |
| NC123S I, Sw-5 | 2.0 | | | | | | | | | | | | P | Q |
| Piedmont | 1.5 | | | | | | | | | | | | | Q |

Example 3

Acylsugar Hybrids

A series of hybrids were created by crossing acylsugar lines with other acylsugar lines. Not all of the crosses produced seed, showing that some of the lines are more advanced than others in the elimination of genes affecting seed and fruit set. Some of the crosses involved backcrosses of newer acylsugar lines to the original line, 97FL, which has the highest acylsugar level and the higher content of *L. pennellii* genome.

Table 4 shows the acylsucrose levels in hybrids created using 97FL as the male parent. In Table 4, column 1 shows the hybrid, column 2 shows the mean acylsugar concentration in μmol/mg dry leaf tissue and column 3 through 9 show the statistical relationship between the acylsugar concentrations of the various hybrids. Levels not connected by same letter are significantly different.

TABLE 4

Acylsucrose levels in hybrids created using 97FL as the male parent

| Pedigree | Mean acylsugar level μmol/mg dried leaf tissue | | | | | | |
|---|---|---|---|---|---|---|---|
| 071026 × 97FL | 42.7 | A | | | | | |
| 066059-2 × 97FL | 41.9 | A | | | | | |
| 066242-7 × 97FL | 33.0 | | B | | | | |
| 071023 × 97FL | 32.1 | | B | C | | | |
| 071024 × 97FL | 29.4 | | B | C | | | |
| 071026 | 25.8 | | | C | D | | |
| 66059-2 | 20.1 | | | | D | | |
| 066254-7 ('071024) | 12.0 | | | | | E | |
| 066062-7 ('071023) | 9.4 | | | | | E | F |
| 071029-1 × 97FL | 5.6 | | | | | | F | G |
| 071028-1 × 97FL | 4.1 | | | | | | F | G |
| 71029; FLA 595-2 Ty | 2.8 | | | | | | | G |

TABLE 4-continued

Acylsucrose levels in hybrids created using 97FL as the male parent

| Pedigree | Mean acylsugar level μmol/mg dried leaf tissue | |
|---|---|---|
| 071028 NC123S I, I2, I3, Ve, Mi, Sw-5 | 2.0 | G |

As shown in Table 4, the hybrids of the control cross, tomato×97FL, have levels of acylsugars that are higher than that of control. The acylsugar levels of all of the hybrids created by crossing an acylsugar line with 97FL are much higher than that of the tomato×97FL controls, ranging from 29 to 43 μmol/mg dry leaf tissue. This demonstrates the impact on acylsugar level of homozygosity for some of the introgressions carried by the acylsugar line female parent. These acylsugar line×97FL hybrids have higher levels of acylsugars than the lines tested in Florida in 2007, and should have superior pest control. Also of interest is the pattern of acylsugar levels among the acylsugar lines and their hybrids with 97FL. The two acylsugar lines 071026 and 66059-2, with acylsugar levels significantly higher than acylsugar lines '071024 and '071023, also produce hybrids with 97FL that have significantly higher acylsugar levels than the parallel hybrids with '071024 and '071023.

Additional crosses were made between various pairs of acylsugar lines. The crosses of some of these lines with 97FL are included in Table 5 for comparative purposes. Table 5 shows the mean acylsugar concentrations in various hybrids in μmol/mg of dried leaf tissue. Column 1 shows the hybrid or line, column 2 shows the acylsugar concentration in μmol/mg of dried leaf tissue and columns 3 through 12 show the statistical relationship between the various hybrids or lines. Levels not connected by same letter are significantly different.

TABLE 5

Total acylsugar levels in hybrids created by crosses of pairs of acylsugar lines

| ID and Types of crosses | Mean acylsugar level μmol/mg dried leaf tissue | | | | | | |
|---|---|---|---|---|---|---|---|
| 071026-7 × 97FL | 42.7 | A | | | | | |
| 066059-2 × 97FL | 41.9 | A | | | | | |
| 071023-2 × 97FL | 32.1 | | B | | | | |
| 071024-3 × 97FL | 29.4 | | B | C | | | |
| 071026 × 066059-2 | 27.2 | | B | C | | | |
| 071026 | 25.8 | | B | C | D | | |
| '071025 × 066060-5 | 23.6 | | B | C | D | E | F |
| 071026 × '071025 | 23.4 | | | C | D | E | |
| 066059-2 × 071025 | 22.9 | | | C | D | E | |
| 071026 × 066060-5 | 20.1 | | | | D | E | F |
| 66059-2 | 20.1 | | | | D | E | F |
| 066059-2 × 071021 | 19.8 | | | | D | E | F |

TABLE 5-continued

Total acylsugar levels in hybrids created by crosses of pairs of acylsugar lines

| ID and Types of crosses | Mean acylsugar level μmol/mg dried leaf tissue | | | | | | | | |
|---|---|---|---|---|---|---|---|---|---|
| 071024 × 066060-5 | 19.1 | C | D | E | F | G | H | I | |
| 071025 | 18.5 | C | D | E | F | G | H | I | J |
| 071026 × 071021 | 18.3 | | | E | F | G | | | |
| 071026 × 071023 | 18.0 | | | E | F | G | H | | |
| 071024 × 071021 | 17.6 | | | E | F | G | H | | |
| 071025 × 071023 | 17.3 | | | E | F | G | H | I | J |
| 071023 × 071021 | 14.7 | | | | F | G | H | I | J |
| 071023 × 066060-5 | 12.0 | | | | | G | H | I | J |
| '071024 | 12.0 | | | | | | H | I | J |
| '071021 | 9.8 | | | | | | | I | J |
| 66060-5 | 9.8 | | | | | | | I | J |
| '071023 | 9.4 | | | | | | | | J |

The crosses to 97FL have higher acylsugar levels than all of the acylsugar line×acylsugar line hybrids. Again, patterns for alteration of acylsugar levels emerge. For example, the two hybrids with 97FL that produced the highest acylsugar levels are those with 071026 and 066059-2 as female parents, and the acylsugar×acylsugar cross with highest acylsugar level is the cross of these two lines. The hybrid created by crossing 071026 and 066059-2 had an acylsugar level roughly 30% lower than that of either of these lines×97FL, but not statistically different from the hybrid of either 071023 or 071024 and 97FL. This shows that 97FL has at least one region not possessed by any of the other lines used in acylsugar×acylsugar crosses, or some combination of interactive introgressions not present in any of the other lines, so that it is unique in its high acylsugar level as a line and as a parent of hybrids. It also shows that 071026 and 066059-2 have at least one region, some combination of interactive introgressions, not possessed by any of the other newer acylsugar lines that results in the higher acylsugar levels in their hybrids with 97FL.

A series of hybrids were also made using *L. pennellii* LA716 as the male parent. Table 6 shows the acylsucrose concentration for tomato hybrids created using *L. pennellii* accession LA716 as the male parent. Column 1 shows the hybrid or line, column 2 shows the mean acylsucrose concentration in μmol/mg of dried leaf tissue, columns 3 through 8 show the statistical relationship between the hybrids or lines and column 9 shows the percent acylglucose relative to total acylsugars found in each hybrid or line. Levels not connected by same letter are significantly different.

TABLE 6

Acylsucrose levels in hybrids created using *L. pennellii* LA716 as the male parent

| Pedigree | Mean acylsugar level μmol/mg dried leaf tissue | | | | | | % acylglucose |
|---|---|---|---|---|---|---|---|
| 071026 × LA716 long internode | 219.2 | A | | | | | 31.5% |
| 071021 × LA716 long internode | 212.1 | A | B | | | | 40.1% |
| 066060 × LA716 long internode | 196.4 | | B | | | | 34.5% |
| 071024 × LA716 long internode | 147.4 | | | C | | | 35.1% |
| NC33EB-1 × LA716 long internode | 39.4 | | | | D | | 31.2% |
| NC84-173 × LA716 long internode | 32.0 | | | | D | | 33.0% |
| acylsugar line '071026 | 25.8 | | | | D | E | |
| acylsugar line '071024 | 12.0 | | | | | E | F | 1.9% |
| acylsugar line '066060-5 | 9.8 | | | | | E | F | 11.3% |
| acylsugar line '071021 | 9.8 | | | | | E | F | 2.8% |
| NC84-173 | 3.6 | | | | | | F | |
| NC33EB-1 (PH-2 + PH-3) | 3.0 | | | | | | F | 13.5% |

As shown in Table 6, the cross of tomato and *L. pennellii* LA716 produced a moderate level of acylsugars similar to some of the acylsugar lines, and roughly ⅛ of that of *L. pennellii* LA716 itself. The cross of acylsugar lines with *L. pennellii* LA716 resulted in markedly higher acylsugar levels, up to ⅔ that of *L. pennellii* LA716. This contrast shows that homozygosity for some region(s) carried in the acylsugar lines is important for the production of higher acylsugar levels in hybrids with *L. pennellii* LA716. That the acylsugar level is so much higher than that of 97FL indicates that at least one region not carried in 97FL but present in *L. pennellii* LA716 exists, and that this region(s) acts in the heterozygous condition to substantially raise acylsugar level. Some of these hybrids were backcrossed to their acylsugar line parent to create backcross populations for mapping and transferring this additional region.

Two of the acylsugar lines were crossed both to 97FL and to *L. pennellii* LA716, allowing a direct comparison of the impact of these two types of crosses on acylsugar levels. Table 7 shows the acylsugar levels in paired hybrids created using the tomato/*L. pennellii* hybrid 97FL and the *L. pennellii* accession LA716 as the male parents. Column 1 shows the hybrid or line, column 2 shows the mean acylsugar concentration in μmol/mg dried leaf tissue and columns 3 through 6 show the statistical relationship between the hybrids. Levels not connected by same letter are significantly different.

TABLE 7

Acylsugar levels in paired hybrids created using 97FL and *L. pennellii* LA716 as the male parents

| Pedigree | Mean acylsugar level μmol/mg dried leaf tissue | | | |
|---|---|---|---|---|
| 071026 × LA716 long internode | 219.2 | A | | |
| 071024 × LA716 long internode | 147.4 | | B | |
| 071026 × 97FL | 42.7 | | | C |
| 071024 × 97FL | 29.4 | | | C D |
| 071026 | 25.8 | | | C D |
| 071024 | 12.0 | | | D |

As shown in Table 7, the cross of either acylsugar line with 97FL raised the acylsugar level compared to that of the acylsugar line parent, but showed a substantially greater increase in acylsugar production in the cross with LA716. The acylsugar line with the lower acylsugar level, as a line, also has the lower acylsugar level in the cross with LA716, and with 97FL.

Example 4

Increase Acylsugar Levels in Tomato

In 2007, the $F_1$ hybrid of two acylsugar lines, 066076-4 (in field as 088006) and 071026 (in field in rows 88001, 88005), had an unexpectedly higher acylsugar level than either of the parents. The two lines have slightly different subsets of *L. pennellii* introgressions, including a modification of the chromosome 3 introgression. The $F_2$ population derived from selfing the (066076-4×071026) $F_1$ was examined to determine if plants with higher acylsugar levels, superior fruit set, and crossability of the 071026 parent can be selected.

The results of the acylsugar tests are in Table 8. In Table 8, the mean acylsugar concentration for an $F_2$ tomato comprising certain introgressions from *L. pennellii* compared to an $F_1$ hybrid and the parent plants are shown. Column 1 shows the row numbers in the trial field, column 2 shows the plant, column 3 shows the seed source for the plant, column 4 shows the average acylsucrose content in μmol/mg of dried leaf tissue, and columns 5 and 6 show the statistical relationship between the plants tested. Levels not connected by same letter are significantly different at the 0.05 level by Tukey test.

TABLE 8

Acylsucrose means for $F_2$ population 088003 and neighboring controls, field Ithaca, summer 2008

| Row numbers | Entry | Seed source | Average Acylsucroses (μmol/mg dry tissue) | |
|---|---|---|---|---|
| 88002, 88004 | F1 hybrid | 071026-5 × 066076-4 | 50.0 | A |
| 088003 | F2 population | 77054-1 | 39.5 | B |
| 088001, 88005, | 071026 parent | 77048-4 | 36.4 | B |
| 88006 | 066076-4 parent | 77044-3 | 28.5 | B |

As shown in Table 8, the 2008 data confirms that the (066076-4×071026) $F_1$ plants had significantly higher acylsugar levels than that of either parents, and that the mean of the $F_2$ populations is similar or slightly higher than that of the higher acylsugar parent, 071026. The results show that the $F_1$ is again significantly higher than either parent. The mean of the $F_2$ population is also somewhat higher than that of both parents, however that is not significant.

Most of the newer acylsugar lines do not cross well with tomato/*L. pennellii* hybrid 97FL, due to reproductive issues of 97FL. However some of the new lines can be crossed with 97FL, and the resulting $F_1$s have the highest levels of acylsugars in crosses between acylsugar lines in the 2007 trials.

The results of the acylsugar tests are provided in Table 9. Table 9 shows the acylsucrose concentration in μmol/mg dried leaf tissue for the $F_2$ population derived from the selfing of (071026×97FL) $F_1$. Column 1 shows the row numbers in the field trial, column 2 shows the plant, column 3 shows the seed source for the plant, column 4 shows the number of plants tested, column 5 shows the average acylsucrose content in μmol/mg of dried leaf tissue, and column 6 shows the standard error.

TABLE 9

Acylsugar levels in 071026 and (071026 × 97FL) $F_2$ population.

| Row numbers | Entries | Seed source | Number plants | Acylsucroses (μmol/mg dry tissue) | |
|---|---|---|---|---|---|
| | | | | Average | Std Err Mean |
| 088001, 088005, 088036 | 071026 parent | 77048-4 | 20 | 38.4212 | 1.0916 |
| 088037 | (071026 × 97FL) $F_1$ rows 088037 | 77071-3 | 228 | 59.0223 | 1.2585 |

As shown in Table 9, the 2008 data shows that the mean of the $F_2$ populations is significantly higher (P<0.0001) than that of the newer acylsugar line parent, 071026. This is because many of the $F_2$ plants have considerably higher acylsugars levels than that of the parental line.

Example 5

Altering Acylsugar Type and Increasing Acylsugar Level

In prior work, examination of multiple accessions of *L. pennellii* showed that accessions either produced a preponderance of acylglucose, or a roughly equal mix of acylsucrose and acylglucose. *L. pennellii* LA716 is an accession producing nearly all acylglucose. However tomato lines bred from LA716 produce only acylsucrose. There is an unexpected tendency among *L. pennellii* accessions that production of acylglucose, rather than acylsucrose, increases acylsugar levels. Perhaps this is due to the different levels of energy that would be required to produce acylglucose rather than acylsucrose. Prior work also unexpectedly showed that crosses between acylsugar lines and *L. pennellii* produce a mix of acylglucose and produced acylsugar levels as high as many *L. pennellii* accessions (but lower than LA716). Therefore the transfer of the QTL associated with acylglucose production might raise acylsugar levels. Seed of several backcross population acylsugar line×(acylsugar line×*L. pennellii* LA716) have been produced, with a different acylsugar line being used in the production of each backcross population. Seed for the related $F_2$ populations were also produced by selfing the $F_1$s. Modest populations of one $BC_1F_1$ and $F_2$ population set were grown during 2007/2008 under greenhouse conditions.

Acylsugar analysis showed that the $BC_1F_1$ and $F_2$ populations unexpectedly both segregate for the ability to produce acylglucoses, and that for plants to produce acylglucoses they must be at least heterozygous for two acylglucose QTL, one on the bottom of chromosome 3 and the other in the middle of chromosome 11. The analysis also unexpectedly showed segregation for plants with much higher acylsugar levels than that of the recurrent acylsugar parent.

Example 6

Testing Acylsugar Lines and Hybrids for Impact on Tomato Spotted Wilt Virus

Acylsugars are found in the green, above-ground parts of *L. pennellii* and the acylsugar lines. Acylsugars are not found in flowers, petals, anthers, or other parts of flowers. Thrips is a pest which feeds on flowers and is very difficult to control. Furthermore, thrips are persistent transmitters of viruses such as tomato spotted wilt virus (TSWV). Therefore it was highly unexpected to find an effect of acylsugars during a test of lines only possessing acylsugar production (not spotted wilt resistance genes) in North Carolina. Table 10 shows the results of the trial. Column 1 shows the variety or line being tested, column 2 shows the number of thrips per 10 leaflets, column 3 shows the number of visual symptoms of viral infection in the plant, column 4 shows the results of ELISA testing for the presence of TSWV, column 5 shows the number of plants tested, column 6 shows the percentage of plants with symptoms, column 7 shows the percentage of plants with a positive ELISA test, column 8 shows the total acylsugar content in µmol/mg of dry tissue, columns 9 through 11 show the statistical relationship between the lines, column 12 shows the percentage of acylsugars for each line, and columns 13 through 15 show the statistical relationship between the lines. Levels not connected by same letter are significantly different at the 0.05 level by Tukey test.

Example 7

Breaking Introgressions to Eliminate Linkage Drag

Some of the *L. pennellii* introgressions in the tomato acylsugar lines are large, and carry genes that are detrimental to horticultural characters. In its original form, the introgression on chromosome 3 covers two-thirds of that chromosome and is associated with poor fruit set, late maturity, small fruit size, and yellow fruit. A tomato hybrid plant heterozygous for a recombinant form of the chromosome 3 introgression has been isolated in an $F_2$ population used for production of the SW5/acylsugar line. That plant has greatly increased fruit set, fruit size, earlier maturity, and is red-fruited.

Example 8

Acylsugar-Producing Tomato Lines

The tomato breeding program generated acylsugar-producing tomato lines to confer broad-spectrum acylsugar-mediated insect resistance to tomato. Five additional lines were produced from crosses of the line acylsugar lines 071026 and 088006. The two parental lines differed for the presence or size of three introgressions, allowing creation of new lines through the segregation for these three introgressions by marker analysis. The five new lines, and some of the lines released previously, were grown together in a greenhouse during spring and summer of 2009 to produce seed under controlled conditions and to test acylsugar levels in greenhouse conditions where higher temperatures maximized acylsugar levels (Table 11).

Some of the lines listed in Table 11 are clearly superior for use in breeding for acylsugar production. We have used the acylsugar line 071026 in further breeding, such as the production of acylsugar lines with virus resistance genes. This line possesses levels of acylsugar that clearly impact insects,

TABLE 10

Number of Thrips, TSWV data, and Acylsugar levels from NC 2008 trial

| Variety/Line | Thrips/10 leaflets Jun. 11, 2008 | # visual symptoms | ELISA+ | # tested | % Symp | % ELISA+ | Total acylsugar (µmol/mg dry tissue) | | % Acylglucose | |
|---|---|---|---|---|---|---|---|---|---|---|
| NC33EB-1 | 41.0abc | 8.50 | 9.00 | 9.75 | 86.94 | 92.22 | 27.4 | C | 64.3 | |
| NC33EB-1 × pennellii | 30.0ab | 2.25 | 5.00 | 9.75 | 23.06 | 51.39 | 69.0 | B | 47.4 | B |
| 071026 | 90.3cd | 8.50 | 8.50 | 9.25 | 91.67 | 91.67 | 67.6 | B | 32.7 | C |
| 071026 × pennellii | 18.3a | 1.50 | 5.00 | 10.00 | 15.00 | 50.00 | 379.6 | A | 55.7 | A |
| 66046-6 | 135.5d | 8.00 | 8.75 | 9.00 | 89.72 | 97.50 | 60.7 | B | 45.2 | B |
| 66046-6 × 97FL | 86.0cd | 5.25 | 6.00 | 9.00 | 58.73 | 66.51 | 75.4 | B | 34.6 | C |

As shown in Table 10, the results unexpectedly showed a sharp decrease in the number of thrips present, as well as an unexpected reduction in detection of TSWV in the plants to 50% of the tomato control. This is very encouraging for the prospect of suppression of thrips and TSWV through use of lines that possess high levels of acylsugar production and one or more virus resistance genes. The combination of the acylsugar mediated insect resistance and specific virus resistance genes could be a combination that will also extend the useful life of the virus resistance genes.

and produces seed well, and only has 4 introgressions from *L. pennellii*. The tomato lines with lower acylsugars levels are of academic interest for studies of relative function, but are not recommended for breeding.

Table 11 shows old and new lines tested in 2009 for acylsugar content. The first column shows the line, column 2 shows acylsugar content to the left, and significantly associated acylsugar levels grouped by letter on the right. Columns 3-39 indicate markers tested in the lines and the homozygous alleles present for each marker, indicating either tomato DNA (designated 1) or *L. pennellii* DNA (designated 3). Levels of acylsugars not connected by same letter are significantly different at the 0.05 level by Tukey-Kramer HSD test.

TABLE 11

Acylsugar levels in greenhouse planting of acylsugar lines for seed increase

| New line or No. of lines in last years release | 2009 GH Total acylsugar (mmol/gm dry tissue) | 2.143 TG154 | 3.015 CLTP5E7 | 3.033 TG130 | 3.047 T1388 | 3.0480 T0677 | 3.053 c2_at4g35930 | 3.0545 TG605 | 3.0590 T1540 | 3.061 clpt21E21 |
|---|---|---|---|---|---|---|---|---|---|---|
| new | 188.5 A | 3 | 1 | 3 | 3 |   | 3 |   |   | 3 |
| new | 170.4 AB | 3 | 1 | 3 | 3 |   | 3 |   |   | 3 |
| 088001 (071026) | 165.8 ABC | 3 | 1 | 3 | 3 |   | 3 |   |   | 3 |
| 88019 | 152.8 ABCD | 3 | 1 | 3 | 3 | 3 |   | 3 | 3 | 3 |
| new | 151.2 ABCDE | 3 | 1 | 1 | 1 |   | 3 |   |   | 3 |
| 88014 | 147.7 BCDE | 3 | 1 | 1 | 1 | 1 |   | 1 | 1 | 3 |
| 88018 | 145.6 BCDE | 3 | 1 | 3 | 3 | 3 |   | 3 | 3 | 3 |
| 88023 | 129.3 CDEF | 3 | 1 | 1 | 1 | 3 |   | 3 | 3 | 3 |
| new | 124.7 DEF | 3 | 1 | 1 | 1 |   | 3 |   |   | 3 |
| 88021 | 113.2 EF | 3 | 1 | 1 | 1 | 3 |   | 3 | 3 | 3 |
| 88006 | 106.6 F | 3 | 1 | 1 | 1 |   |   |   |   | 3 |
| 88022 | 99.7 FG | 3 | 1 | 1 | 1 | 3 |   | 3 | 3 | 3 |
| new | 96.5 FG | 3 | 1 | 1 | 1 |   | 3 |   |   | 3 |

| New line or No. of lines in last years release | 3.0727 At3g03100 | 3.074 ssr111 | 3.099 ssr22 | 3.1025 c2_at5g23060 | 4.014 SSR 43 | 4.022 TG370 | 5.008 TG623 | 5.019 TG441 | 5.024 SSR13 | 5.026 c2_at2G01410 |
|---|---|---|---|---|---|---|---|---|---|---|
| new | 3 | 3 | 3 | 3 |   | 1 | 1 | 1 |   | 1 |
| new | 3 | 3 | 3 | 3 |   | 3 | 1 | 1 |   | 1 |
| 088001 (071026) | 3 | 3 | 3 | 3 | 1 | 1 | 1 | 1 | 1 | 1 |
| 88019 | 3 | 3 | 3 |   | 1 | 1 | 1 | 1 | 1 |   |
| new | 3 | 3 | 3 | 3 |   | 1 | 1 | 1 |   | 1 |
| 88014 |   | 3 | 3 |   | 1 | 1 | 1 | 1 | 1 |   |
| 88018 |   | 3 | 3 |   | 1 | 1 | 1 | 1 | 1 |   |
| 88023 |   | 3 | 3 |   | 3 | 3 | 3 | 3 | 3 |   |
| new | 3 | 3 | 3 | 3 |   | 3 | 3 | 3 |   | 3 |
| 88021 |   | 3 | 3 |   | 1 | 1 | 1 | 1 | 1 |   |
| 88006 | 3 | 3 | 3 |   | 3 | 3 | 3 | 3 | 3 |   |
| 88022 |   | 3 | 3 |   | 3 | 3 | 3 | 3 | 3 |   |
| new | 3 | 3 | 3 | 3 |   | 3 | 1 | 1 |   | 1 |

| New line or No. of lines in last years release | 5.035 SSR115 | ca 5.047 TG503 | 5.044 At3g55120 | 5.051 At4g24830 | 5.062 Pto | 5.0625 c2_at24690 | 7.0640 TG20 | 7.0680 c2_at3g15430 | 8.050 SSR335 |
|---|---|---|---|---|---|---|---|---|---|
| new | 1 | 1 | 1 |   | 1 |   | 3 |   | 1 |
| new | 1 | 1 | 1 |   | 1 |   | 3 |   | 1 |
| 088001 (071026) | 1 | 1 | 1 | 1 | 1 |   | 3 |   | 1 |
| 88019 | 1 |   | 3 |   | 3 |   | 3 | 3 | 1 |
| new | 1 | 1 | 1 |   | 1 |   | 3 |   | 1 |
| 88014 | 1 |   | 1 |   |   |   | 3 | 3 | 1 |
| 88018 | 1 |   | 3 |   |   |   | 3 | 3 | 1 |
| 88023 | 3 |   | 3 | 3 | 3 | 3 | 3 | 3 | 3 |
| new | 3 | 3 | 3 |   | 3 |   | 3 |   | 1 |
| 88021 | 1 |   | 1 | 1 | 1 | 1 | 3 | 3 | 3 |
| 88006 | 3 | 3 | 3 |   | 3 | 3 | 3 |   | 1 |
| 88022 | 3 |   | 3 | 3 | 3 | 3 | 3 | 3 | 1 |
| new | 1 | 1 | 1 |   | 1 |   | 3 |   | 1 |

| New line or No. of lines in last years release | 8.055 SSR 38 | 8.067 CT148 | 10.000 TG230 | 10.011 TG303 | 10.028 SSR34 | 10.035 SSR 248 | ca 10.035 pXagt | 10.039 At3g08760 | 10.055 SSR85 |
|---|---|---|---|---|---|---|---|---|---|
| new | 1 | 1 | 3 | 3 | 1 | 1 | 1 | 1 | 3 |
| new | 1 | 1 | 3 | 3 | 1 | 1 | 1 | 1 | 3 |
| 088001 (071026) | 1 | 1 | 3 | 3 | 1 | 1 | 1 | 1 | 3 |
| 88019 | 1 | 1 | 3 | 3 | 1 | 1 | 1 | 1 | 3 |

TABLE 11-continued

Acylsugar levels in greenhouse planting of acylsugar lines for seed increase

| | | | | | | | | | |
|---|---|---|---|---|---|---|---|---|---|
| new | 1 | 1 | 3 | 3 | 1 | 1 | 1 | 1 | 3 |
| 88014 | 1 | 1 | | 1 | 3 | 3 | 3 | | 3 |
| 88018 | 1 | 1 | | 3 | 1 | 1 | 1 | | 3 |
| 88023 | 3 | 3 | | 3 | 1 | 1 | 1 | | 3 |
| new | 1 | 1 | 3 | 3 | 1 | 1 | 1 | 1 | 3 |
| 88021 | 3 | 3 | | 3 | 1 | 1 | 1 | | 3 |
| 88006 | 1 | 1 | 3 | 3 | 1 | 1 | 1 | 1 | |
| 88022 | 1 | 1 | | 3 | 1 | 1 | 1 | | 3 |
| new | 1 | 1 | 3 | 3 | 1 | 1 | 1 | 1 | 3 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the tomato seed of this invention is maintained by Cornell University, 20 Thornwood Drive, Suite 105, Ithaca, N.Y. 14850. Applicant has also deposited seed of the invention with the American Type Culture Collection (ATCC), Manassas, Va., in compliance with the Budapest Treaty, complies with 37 C.F.R. §1.801-§1.809. The ATCC Accession No. is PTA-11474. Access to this deposit will be available during the pendency of this application to persons determined by the Commissioner of Patents and Trademarks to be entitled thereto under 37 CFR §1.14 and 35 USC §122.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A tomato seed, representative-seed having been deposited under ATCC Accession No. PTA-11474.

2. A plant grown from the tomato seed of claim 1.

3. A plant part of the tomato plant of claim 2.

4. A tissue culture of the tomato plant of claim 2.

* * * * *